United States Patent [19]

Kolts et al.

[11] Patent Number: 4,705,769
[45] Date of Patent: Nov. 10, 1987

[54] COMPOSITION OF MATTER FOR CONVERSION OF $C_3$ AND $C_4$ HYDROCARBONS

[75] Inventors: John H. Kolts, Ochelata; Gary A. Delzer, Bartlesville, both of Okla.

[73] Assignee: Phillips Petroleum Company, Bartlesville, Okla.

[21] Appl. No.: 902,801

[22] Filed: Jul. 31, 1986

Related U.S. Application Data

[62] Division of Ser. No. 758,938, Jul. 25, 1985, Pat. No. 4,621,162.

[51] Int. Cl.$^4$ .................. B01J 21/04; B01J 21/06; B01J 21/10; B01J 23/02; B01J 23/26; B01J 23/34; B01J 23/74
[52] U.S. Cl. ........................ 502/241; 502/251; 502/324; 502/328
[58] Field of Search ............ 502/241, 251, 324, 328

[56] References Cited

U.S. PATENT DOCUMENTS 2,395,875  3/1946  Kearby .................. 502/328 X

FOREIGN PATENT DOCUMENTS 2115860  10/1972  Fed. Rep. of Germany ...... 502/328
1306087  2/1973  United Kingdom ................ 585/651
199837  7/1967  U.S.S.R. ............................ 502/324

*Primary Examiner*—W. J. Shine
*Attorney, Agent, or Firm*—French and Doescher

[57] ABSTRACT

Compositions of matter comprise oxides of silicon, aluminum and/or titanium mixed with combinations of manganese oxide and magnesium oxide; iron oxide and magnesium oxide; calcium, strontium, barium, tin and/or antimony oxides, manganese oxide and magnesium oxide; and iron oxide, manganese oxide and magnesium oxide. These compositions are particularly useful as catalysts for selectively converting propane and butanes to ethylene and ethane and particularly to ethylene. A method for converting propane and butanes to less saturated hydrocarbons is also disclosed in which the catalyst life is extended and the selectivity to ethylene and ethane, particularly ethylene, is improved by carrying out the contacting with the catalyst in the presence of steam, when the catalyst contains an oxide of iron and, optionally, when the catalyst does not contain an oxide of iron.

16 Claims, No Drawings

COMPOSITION OF MATTER FOR CONVERSION OF $C_3$ AND $C_4$ HYDROCARBONS

This application is a Division of application Ser. No. 758,938, filed July 25, 1985, now U.S. Pat. No. 4,621,162.

The present invention relates to improved compositions of matter. In a more specific aspect, the present invention relates to improved catalysts for the conversion of $C_3$ and $C_4$ hydrocarbons to less saturated hydrocarbons. In a more specific aspect, the present invention relates to improved catalysts for the conversion of $C_3$ and $C_4$ alkanes to less saturated hydrocarbons, particularly ethylene and propylene and preferably ethylene.

BACKGROUND OF THE INVENTION

Olefins, such as ethylene and propylene have become major feedstocks in the organic chemical and the petrochemical industries. Of these, ethylene is by far the most important chemical feedstock, since the requirements for ethylene feedstocks are about double those for propylene feedstocks. Consequently, improved methods for the conversion of less valuable hydrocarbons to ethylene and propylene, and particularly to ethylene, are highly desirable.

Numerous suggestions have been made for the production of ethylene and propylene, particularly ethylene, from various feedstocks and by a wide variety of processes.

At the present time, ethylene is produced almost exclusively by dehydrogenation or thermal cracking of ethane and propane, naphtha and, in some instances, gas oils. About 75% of the ethylene currently in the United States is produced by steam cracking of ethane and higher normally gaseous hydrocarbon components of natural gas, since natural gas contains about 5 volume percent to about 60 volume percent of hydrocarbons other than methane. However, in most instances, the content of ethane and higher normally gaseous hydrocarbon materials in natural gas is less than about 25% and usually less than about 15%. Consequently, these limited quantities of feedstock, which are available for the production of ethylene and propylene, and particularly ethylene, must be utilized efficiently. Unfortunately, these processes result in low conversions to olefins and selectivity to ethylene, as opposed to propylene, is poor. In addition, relatively severe conditions, particularly temperatures in excess of 1000° C., are required and such processes are highly energy intensive.

In order to reduce the severity of the conditions and, more importantly, to improve the conversion of normally gaseous feedstocks to ethylene and propylene and selectively to ethylene, numerous processes involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use of solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective, or why certain combinations of components are effective and other combinations are not. Obviously, a number of theories have been proposed by workers in the art, but this only adds to the confusion, since it appears that each theory explains why a particular material works well, but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide improved compositions of matter and methods of utilizing the same, which overcome the above and other disadvantages of the prior art. Another object of the present invention is to provide improved compositions of matter. Still another object of the present invention is to provide improved catalytic compositions for the conversion of $C_3$ and $C_4$ hydrocarbons to less saturated hydrocarbons. Another and further object of the present invention is to provide an improved method for the conversion of $C_3$ and $C_4$ hydrocarbons to less saturated hydrocarbons, in the presence of steam. Yet another object of the present invention is to provide an improved process for the conversion of $C_3$ and $C_4$ hydrocarbons to less saturated hydrocarbons, in the presence of steam, to selectively produce ethylene, ethane and propylene, and particularly ethylene. A further object of the present invention is to provide an improved catalytic material for the conversion of $C_3$ and $C_4$ hydrocarbons to less saturated hydrocarbons, which has an improved effective life, before regeneration is necessary, particularly for the production of ethylene, ethane and propylene, and more particularly ethylene.

The present invention provides improved compositions of matter, including:

a composition comprising at least one oxide of silicon, aluminum and/or titanium, at least one oxide of manganese and at least one oxide of magnesium;

a composition comprising at least one oxide of silicon, aluminum and/or titanium, at least one oxide of calcium, strontium, barium, tin and/or antimony, at least one oxide of manganese and at least one oxide of magnesium;

a composition comprising at least one oxide of silicon, aluminum and/or titanium, at least one oxide of iron and at least one oxide of magnesium; and a composition comprising at least one oxide of silicon, aluminum and/or titanium, at least one oxide of iron, at least one oxide of manganese and at least one oxide of magnesium.

These compositions of matter have been found to be highly effective catalytic compositions for the conversion of feed hydrocarbons comprising at least one of $C_3$ and $C_4$ hydrocarbons to less saturated hydrocarbons, preferably in the presence of steam. A method of converting feed hydrocarbons comprising $C_3$ and $C_4$ hydrocarbons to less saturated hydrocarbons, particularly ethylene and propylene and preferably ethylene, is provided in which the feed hydrocarbons are contacted with the above-mentioned catalytic compositions, preferably in the presence of steam, under conditions sufficient to convert the feed hydrocarbons to less saturated hydrocarbons. The effectiveness of the catalytic compositions is also improved by limiting the sulfur content thereof.

DETAILED DESCRIPTION OF THE INVENTION

The hydrocarbon feed components, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that if isobutane is utilized, in accordance with the present invention, the catalysts of the present invention shift the product stream from isobutene to propylene and, therefore, one of the desired products of the present invention is produced. On the other hand, it has been found that the catalytic process of the present invention is generally ineffective, as compared with a strictly thermal process, in improving the conversion of ethane to ethylene. However, the presence of ethane in feed hydrocarbons, obviously, is not detrimental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention. Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6$+hydrocarbons or natural gasoline), then $C_5$, followed by $C_4$, then $C_3$ and, finally, $C_2$ hydrocarbons, by cooling to successively lower temperatures with separation or fractionation of the condensed liquid from uncondensed vapor between cooling stages. Thus, individual streams predominating in an individual hydrocarbon, such as $C_5$, $C_4$, $C_3$ and $C_2$, can be obtained or streams predominating in combinations of the individual hydrocarbons can be recovered. Accordingly, the thus separated propane stream or the thus separated butanes stream can be utilized as feed hydrocarbons for the present invention, or a stream predominating in a mixture of propane and butanes can be utilized. Obviously, the latter would eliminate the necessity of one stage of cooling and separation in a natural gas processing system.

The compositions of matter of the present invention include:

A composition comprising at least one oxide of silicon, aluminum and/or titanium, at least one oxide of manganese and at least one oxide of magnesium; a composition comprising at least one oxide of silicon, aluminum and/or titanium, at least one oxide of calcium, strontium, barium, tin and/or antimony, at least one oxide of manganese and at least one oxide of magnesium; a composition comprising at least one oxide of silicon, aluminum and/or titanium, at least one oxide of iron and at least one oxide of magnesium; and a composition comprising at least one oxide of silicon, aluminum and/or titanium, at least one oxide of iron, at least one oxide of manganese and at least one oxide of magnesium. From time to time, herein, the iron oxide and the manganese oxide are referred to as active components and the magnesium oxide as a base material. Similarly, the oxides of silicon, titanium and aluminum, as well as the oxides of calcium, strontium, barium, tin and antimony are referred to as promoters. These references are simply utilized as a matter of convenience, since the magnesium oxide is usually present in a major proportion, whereas the other oxides are present in minor amounts. Accordingly, it is to be understood that such reference is not meant to categorize the components. As will appear hereinafter, when the use of the compositions of matter as catalysts for the process of the present invention is discussed, all of the recited components are necessary and all are catalytically active in the process of the present invention.

The above-mentioned compositions of matter have been found to be particularly effective as catalytic compositions for the conversion of $C_3$ and $C_4$ hydrocarbons to less saturated hydrocarbons. Accordingly, for such use, the composition will generally contain from about 0.1 to about 30 wt. % of the components other than the oxides of magnesium, expressed in terms of the element based on the total weight of the composition, and preferably between about 0.5 and about 15 wt. % of the components other than magnesium oxide. Parallel work has shown that oxides of calcium, strontium, barium, tin and antimony are effective promoters for increasing the active life of the catalyst compositions and improving the selectivity to ethylene of catalytic materials which do not contain iron as a component, but that these materials are either ineffective as promoters or are detrimental when present in catalysts containing iron as a component. When these promoting materials are utilized in addition to the oxides of silicon, titanium and aluminum, the combined promoters, obviously, may be present in smaller amounts.

The method of preparation of the catalyst compositions of the present invention does not appear to be critical, so long as the desired final compositions of the component metal oxides is obtained. Suitable methods of preparation include slurry blending, solution blending, dry blending, impregnation and co-precipitation, all of which are well known to those skilled in the art. A convenient method is to add metal solids, such as MgO or Mg(OH)$_2$, of the base material to a blending apparatus along with an aqueous solution of a metal salt, such as Mn(NO$_3$)$_2$, of the active component or the promoter and mixing for several minutes, for example, 2-5 minutes, to form a thick slurry. In the interest of economy, excess water should be avoided. The resulting slurry is then dried in air by conventional means, at about 100° C. to 150° C., calcined for about 4 hours, at about 750° C. to 800° C., and then ground, sieved and, optionally, pelleted or otherwise sized by means well known in the art. Where relatively small amounts of a promoter are utilized, the magnesium oxide base and active component, such as magnesium oxide and iron oxide, are formed by the above slurrying method and the minor amount of promoter is then impregnated on the thus formed material. When utilizing the above-mentioned catalyst compositions containing iron, it has been found, in accordance with another aspect of the present invention, that steam is essential to the conduct of the process. Specifically, the presence of steam, during the conduct of the conversion of $C_3$ and $C_4$ hydrocarbons, greatly extends the active life of the catalyst and it has been found that, without steam, over an extended period of time, the iron oxide reduces to metallic iron, which is ineffective in the process. On the other hand, the catalyst compositions which do not contain iron as a component may be utilized without steam but the presence of steam also extends the active life of the catalyst. Accordingly, when the catalyst composition does not contain iron as a component, the presence of steam is optional.

The process of the present invention can be carried out in fixed, moving, fluidized, ebullating or entrained bed reactors. For experimental purposes and, obviously, to permit accurate and precise control of the process variables, the runs hereinafter set forth in the examples were conducted in a fixed bed reactor.

During operation, in accordance with the present invention, it has been found that small amounts of the feedstock are converted to coke, which is then deposited upon the catalyst and contributes to a decline in the catalyst activity, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperatures, as is also well known to those skilled in the art.

As previously indicated, the presence of steam, during the operation of the process, serves to extend the active life of the catalyst for the conversion of the feed hydrocarbons to less saturated hydrocarbons, and particularly to ethylene production. However, even when steam is present, in the conduct of the reaction, it is generally necessary to regenerate the catalyst in order to maximize the ethylene production. In accordance with the present invention, the promoters comprising oxides of silicon, aluminum and/or titanium greatly increase the active life of the catalytic compositions. This will be shown in the examples hereinafter. As previously indicated, promoters including oxides of calcium, strontium, barium, tin and/or antimony are similarly effective as life-extending promoters, when the ethylene-selective catalysts, which do not contain oxides of iron, are utilized. These life-extending promoters also have the additional advantage of further increasing the selectivity of the catalyst to $C_2$ hydrocarbons, as opposed to propylene, and particularly to ethylene.

Following preparation of the catalytic composition, the catalyst may be prepared for use by purging with an inert gas, such as nitrogen. Normally, the catalyst would be disposed in the reactor and be brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and/or iron and, thereby, reduces initial carbon oxide formation.

With the exception of the presence of steam and the temperature of operation, the operating conditions of the process, in accordance with the present invention, do not appear to be highly critical. Accordingly, the following conditions of operation are those found effective and preferred.

The steam/hydrocarbon mole ratio may be between 0 and about 10/1, for iron-free catalysts, and about 0.1 to 10/1, for iron-containing catalysts, and is preferably between about 0.5/1 and about 5/1.

The hydrocarbon gas hourly space velocity (GHSV) may range from about 100 to about 3000 but is preferably between about 500 and about 1000.

The operating pressure may be between about 0.1 and about 100 psia and is preferably between about 1 and about 60.

The temperature of operation appears to be significant in the conversion of feed hydrocarbons to olefins and particularly in improving the selectivity to ethylene. Suitable temperatures range between about 550° C. and about 850° C., with the preferred range being between about 650° C. and about 775° C.

It is also highly desirable that the "bound" or "fixed" sulfur content of the catalyst compositions be limited. It has been found that excessive amounts of "bound" or "fixed" sulfur have a detrimental effect on the catalyst compositions, to the extent that the selectivity to the production of $C_2$ hydrocarbons is reduced. Such sulfur is referred to as "bound" or "fixed" sulfur since it does not appear to be converted to hydrogen sulfide or be otherwise lost during the conduct of the process or the regeneration step and it is probably present in the form of sulfates. Accordingly, in order to reduce the "bound" or "fixed" sulfur content of the catalyst compositions, it is desirable to select catalyst components which are low in sulfur compounds or to remove such sulfur compounds from the catalyst components before preparing the catalyst or from the catalyst after preparation but before use. The catalyst compositions should contain less than about 0.2 wt. % of sulfur, expressed in terms of elemental sulfur based on the total weight of the catalyst, and preferably less than about 0.1 wt. %.

The nature and advantages of the present invention are illustrated by the following examples.

EXAMPLE I

A series of runs were carried out in which the catalyst compositions of the present invention were compared with quartz chips, which represents a typical thermal, steam cracking process and the conversion and product distribution usually obtained, a run wherein manganese oxide/magnesium oxide alone was utilized and runs in which silicon, aluminum and titanium oxide were utilized as major components or bases of catalyst compositions.

The catalysts, in accordance with the present invention, were prepared by forming the manganese oxide/magnesium oxide by the slurrying method set forth above and, thereafter, impregnating this material with compounds of silicon, aluminum or titanium.

Typical reactor conditions were 25 cc of 16–40 mesh catalyst, n-butane as a feed at 480 GHSV and a steam/hydrocarbon mole ratio of 1/1. The temperatures of operation are set forth in the table which follows. Conversion is expressed in terms of mole percent of n-butane converted and selectivities are also in terms of mole percent of n-butane converted to a particular product.

The results of this series of runs are set forth in the table below.

TABLE I

| Catalyst | Temp. | Conv. | Selectivity | | | $C_2^= + C_2$ |
| | | | $C_2^=$ | $C_3^=$ | $C_2$ | $C_3^=$ |
| --- | --- | --- | --- | --- | --- | --- |
| Quartz Chips Only | 700 | 42 | 30 | 40 | 6 | 0.9 |
| 5% Mn/MgO | 675 | 51 | 35 | 31 | 13 | 1.55 |
| 15% SiO$_2$/5% Mn/MgO | 675 | 53 | 36 | 27 | 18 | 2.00 |
| 15% SiO$_2$/5% Mn/MgO | 715 | 80 | 38 | 22 | 15 | 2.50 |
| 15% Al$_2$O$_3$/5% Mn/MgO | 675 | 62 | 33 | 22 | 25 | 2.64 |
| 15% Al$_2$O$_3$/5% Mn/MgO | 700 | 80 | 34 | 20 | 24 | 2.90 |
| 15% TiO$_2$/5% Mn/MgO | 675 | 53 | 35 | 26 | 18 | 2.04 |
| 15% TiO$_2$/5% Mn/MgO | 705 | 80 | 35 | 23 | 18 | 2.30 |
| 5% Mn/Al$_2$O$_3$—TiO$_2$ | 673 | 50 | 24 | 21 | 14 | 1.81 |
| 3% Ca/3.5% Mn/SiO$_2$ | 702 | 50 | 32 | 39 | 7 | 1.00 |
| 4% Mn/Al$_2$O$_3$ | 710 | 50 | 26 | 28 | 8 | 1.21 |

It is to be observed that the combination of manganese oxide and magnesium oxide substantially increased the selectivity to C$_2$ hydrocarbons and particularly ethylene, as opposed to propylene, when compared with the thermal conversion. On the other hand, the catalyst compositions containing small promoting amounts of oxides of silicon, aluminum and titanium not only increased the conversion of n-butane but increased the selectivity to C$_2$ hydrocarbons substantially and somewhat increased the selectivity to ethylene, as opposed to propylene, when compared with the manganese oxide/magnesium oxide catalyst without the promoters. The promoted catalysts obviously were vastly superior to the thermal conversion. Where silicon, aluminum and titanium were utilized as major components or as base components, it is to be observed that the product distribution is little, if any, better than that obtained by thermal conversion. While the combination of manganese oxide/aluminum oxide-titanium oxide does exhibit a relatively high C$_2$ hydrocarbons to propylene ratio, it is to be oberved that this result is anomolous, to the extent that the production of ethylene was substantially reduced compared to that of the promoted catalyst of the present invention and even compared to the thermal conversion.

EXAMPLE II

In another series of tests, 5% Mn/MgO, prepared by the slurring technique, was impregnated with oxides of silicon, titanium and aluminum for evaluation in the cracking of n-butane at a constant temperature of 675° C. The steam/hydrocarbon mole ratio was 1/1 and the residence time was 1 second, when utilizing 25 cc of catalyst. The results of this series of runs is set forth in the following table.

TABLE II

| Catalyst | Conv. % | Selectivity, % | | | $C_2^= + C_2$ |
| | | $C_2^=$ | $C_3^=$ | $C_2$ | $C_3^=$ |
| --- | --- | --- | --- | --- | --- |
| 5% Mn/MgO | 51 | 35 | 31 | 13 | 1.55 |
| 5% Mn/15% SiO$_2$/MgO | 53 | 36 | 27 | 18 | 2.00 |
| 5% Mn/15% TiO$_2$/MgO | 53 | 35 | 26 | 18 | 2.04 |
| 5% Mn/15% Al$_2$O$_3$/MgO | 62 | 33 | 22 | 25 | 2.64 |

It is to be noted from the above table that the addition of small promoting amounts of oxides of silicon and titanium to the maganese oxide/magnesium oxide catalyst improved the conversion and C$_2$ hydrocarbon selectivity significantly and the addition of the oxide of aluminum was outstanding in effecting these improvements.

EXAMPLE III

In yet another series of tests, n-butane was cracked at 675° C. Hydrocarbon feed was at a rate of 240 GHSV and a steam/hydrocarbon feed ratio of about 1/1 was used. The catalyst comprised 3%Ca/4%Mn/MgO containing varying amounts of Al$_2$O$_3$, prepared by slurry blending followed by impregnation with aluminum. Table III sets forth the results obtained.

TABLE III

| Catalyst % Al$_2$O$_3$ | Conv. % | Selectivity, % | | | $C_2^= + C_2$ |
| | | $C_2^=$ | $C_3^=$ | $C_2$ | $C_3^=$ |
| --- | --- | --- | --- | --- | --- |
| 0 | 45 | 38 | 24 | 24 | 2.58 |
| 0 | 47 | 37 | 24 | 26 | 2.63 |
| 1 | 58 | 40 | 18 | 30 | 3.89 |
| 2 | 48 | 40 | 19 | 28 | 3.58 |
| 5 | 38 | 41 | 20 | 28 | 3.45 |
| 10 | 38 | 40 | 20 | 28 | 3.40 |
| 15 | 36 | 40 | 19 | 28 | 3.58 |

It is to be observed from the above table that the addition of small, promoting amounts of aluminum oxide, significantly improves the selectivity to ethylene and C$_2$ hydrocarbons while reducing the production of propylene. As little as 1 to 2 wt. % of aluminum was found to be particularly effective.

In addition to the advantages shown above, it has been observed, qualitatively, that the addition of alumina also increases the hardness and durability of the catalyst.

While specific materials, conditions of operation, modes of operation and equipment have been referred to herein, it is to be recognized that these and other specific recitals are for illustrative purposes and to set forth the best mode only and are not to be considered limiting.

That which is claimed:

1. A composition of matter selected from the group consisting of:
   (a) a composition consisting essentially of: about 0.1 weight-% to about 30 weight-% of each of (1) at least one oxide of at least one element selected from the group consisting of silicon, aluminum and titanium and (2) at least one oxide of manganese and the balance being (3) at least one oxide of magnesium;
   (b) a composition consisting essentially of: about 0.1 weight-% to about 30 weight-% of each of (1) at least one oxide of at least one element selected from the group consisting of silicon, aluminum and titanium, (2) at least one oxide of at least one metal selected from the group consisting of calcium, strontium, barium, tin and antimony and (3) at least one oxide of manganese and the balance being (4) at least one oxide of magnesium;

(c) a composition consisting essentially of: about 0.1 weight-% to about 30 weight-% of each of (1) at least one oxide of at least one element selected from the group consisting of silicon, aluminum and titanium and (2) at least one oxide of iron and the balance being (3) at least one oxide of magnesium; and (d) a composition consisting essentially of: about 0.1 weight-% to about 30 weight-% of each of (1) at least one oxide of at least one element selected from the group consisting of silicon, aluminum and titanium, (2) at least one oxide of iron and (3) at least one oxide of manganese and the balance being (4) at least one oxide of magnesium.

2. A composition in accordance with claim 1 wherein the at least one oxide of at least one element selected from the group consisting of silicon, aluminum and titanium is at least one oxide of aluminum.

3. A composition in accordance with claim 1 wherein the composition consists essentially of (1) at least one oxide of at least one element selected from the group consisting of silicon, aluminum and titanium, (2) at least one oxide of manganese and (3) at least one oxide of magnesium.

4. A composition in accordance with claim 1 wherein the composition consists essentially of (1) at least one oxide of at least one element selected from the group consisting of silicon, aluminum and titanium, (2) at least one oxide of at least one metal selected from the group consisting of calcium, strontium, barium, tin and antimony, (3) at least one oxide of manganese and (4) at least one oxide of magnesium.

5. A composition in accordance with claim 4 wherein the at least one oxide of calcium, strontium, barium, tin and antimony is at least one oxide of at least one metal selected from the group consisting of calcium, strontium and barium.

6. A composition in accordance with claim 5 wherein the at least one metal selected from the group consisting of calcium, strontium and barium is calcium.

7. A composition in accordance with claim 1 wherein the composition consists essentially of (1) at least one oxide of at least one element selected from the group consisting of silicon, aluminum and titanium, (2) at least one oxide of iron and (3) at least one oxide of magnesium.

8. A composition in accordance with claim 1 wherein the composition consists essentially of (1) at least one oxide of at least one element selected from the group consisting of silicon, aluminum and titanium, (2) at least one oxide of iron, (3) at least one oxide of manganese and (4) at least one oxide of magnesium.

9. A catalyst composition, adapted to convert feed hydrocarbons comprising at least one of $C_3$ and $C_4$ hydrocarbons to less saturated product hydrocarbons, selected from the group consisting of:

(a) a catalyst composition consisting essentially of: about 0.1 weight-% to about 30 weight-% of each of (1) at least one oxide of at least one element selected from the group consisting of silicon, aluminum and titanium and (2) at least one oxide of manganese and the balance being (3) at least one oxide of magnesium;

(b) a catalyst composition consisting essentially of: about 0.1 weight-% to about 30 weight-% of each of (1) at least one oxide of at least one element selected from the group consisting of silicon, aluminum and titanium, (2) at least one oxide of at least one metal selected from the group consisting of calcium, strontium, barium, tin and antimony and (3) at least one oxide of manganese and the balance being (4) at least one oxide of magnesium;

(c) a catalyst composition consisting essentially of: about 0.1 weight-% to about 30 weight-% of each of (1) at least one oxide of at least one element selected from the group consisting of silicon, aluminum and titanium and (2) at least one oxide of iron and the balance being (3) at least one oxide of magnesium; and (d) a catalyst composition consisting essentially of: about 0.1 weight-% to about 30 weight-% of each of (1) at least one oxide of at least one element selected from the group consisting of silicon, aluminum and titanium, (2) at least one oxide of iron and (3) at least one oxide of manganese and the balance being (4) at least one oxide of magnesium.

10. A catalyst composition in accordance with claim 9 wherein the at least one oxide of at least one element selected from the group consisting of silicon, aluminum and titanium is at least one oxide of aluminum.

11. A catalyst composition in accordance with claim 9 wherein the catalyst composition consists essentially of (1) at least one oxide of at least one element selected from the group consisting of silicon, aluminum and titanium, (2) at least one oxide of manganese and (3) at least one oxide of magnesium.

12. A catalyst composition in accordance with claim 9 wherein the catalyst composition consists essentially of (1) at least one oxide of at least one element selected from the group consisting of silicon, aluminum and titanium, (2) at least one oxide of at least one metal selected from the group consisting of calcium, strontium, barium, tin and antimony, (3) at least one oxide of manganese and (4) at least one oxide of magnesium.

13. A catalyst composition in accordance with claim 12 wherein the at least one oxide of calcium, strontium, barium, tin and antimony is at least one oxide of at least one metal selected from the group consisting of calcium, strontium and barium.

14. A catalyst composition in accordance with claim 13 wherein the at least one metal selected from the group consisting of calcium, strontium and barium is calcium.

15. A catalyst composition in accordance with claim 9 wherein the catalyst composition consists essentially of (1) at least one oxide of at least one element selected from the group consisting of silicon, aluminum and titanium, (2) at least one oxide of iron and (3) at least one oxide of magnesium.

16. A catalyst composition in accordance with claim 9 wherein the catalyst composition consists essentially of (1) at least one oxide of at least one element selected from the group consisting of silicon, aluminum and titanium, (2) at least one oxide of iron, (3) at least one oxide of manganese and (4) at least one oxide of magnesium.

* * * * *